United States Patent
Gerhard et al.

(10) Patent No.: US 7,361,921 B2
(45) Date of Patent: Apr. 22, 2008

(54) DEVICE AND METHOD FOR PLANE-PARALLEL ORIENTATION OF A THE SURFACE OF AN OBJECT TO BE EXAMINED IN RELATION TO A FOCUS PLANE OF A LENS

(75) Inventors: Detlef Gerhard, München (DE); Johannes Lechner, München (DE)

(73) Assignee: Icos Vision Systems NV, Heverlee (BE)

( * ) Notice: Subject to any disclaimer, the term of this patent is extended or adjusted under 35 U.S.C. 154(b) by 0 days.

(21) Appl. No.: 10/490,053

(22) Filed: Mar. 19, 2004

(65) Prior Publication Data
US 2005/0072944 A1 Apr. 7, 2005

(30) Foreign Application Priority Data
Sep. 19, 2001 (DE) ................................ 101 46 221

(51) Int. Cl.
*G01R 31/02* (2006.01)
(52) U.S. Cl. ................................ 250/559.4; 250/559.44
(58) Field of Classification Search . 250/559.4–559.44
See application file for complete search history.

(56) References Cited

U.S. PATENT DOCUMENTS

| 4,785,177 A | 11/1988 | Besocke |
| 5,239,355 A | 8/1993 | Hirose |
| 5,410,259 A * | 4/1995 | Fujihara ..................... 324/758 |
| 5,798,195 A * | 8/1998 | Nishi .......................... 430/22 |

\* cited by examiner

*Primary Examiner*—Thanh X. Luu
*Assistant Examiner*—Tony Ko
(74) *Attorney, Agent, or Firm*—Staas & Halsey LLP

(57) ABSTRACT

The orientation of the surface of an object to be examined is changed by adjusting the distance thereof to an optical measuring system in a plane-parallel manner in relation to a focusing plane of the optical measuring system, enabling high speeds of examination to be obtained during examination of the extended surfaces of the object. A distance-measurement system which is mounted in an auxiliary manner with regard to the measuring head enables fluctuations in the topography inside the surface of the object to be compensated in such a way that a currently received point or area can be optically sharpened.

7 Claims, 2 Drawing Sheets

DEVICE AND METHOD FOR PLANE-PARALLEL ORIENTATION OF A THE SURFACE OF AN OBJECT TO BE EXAMINED IN RELATION TO A FOCUS PLANE OF A LENS

CROSS REFERENCE TO RELATED APPLICATIONS

This application is based on and hereby claims priority to German Application No. 10146221.2 filed on Sep. 19, 2001, the contents of which are hereby incorporated by reference.

BACKGROUND OF THE INVENTION

The invention relates to a device and a method, with which, for optical inspection of a flat surface of an object, its plane-parallel orientation to a focus plane of a lens belonging to a measuring head can be achieved. For optical inspection of objects or of object surfaces, such as for example the surface of wafers, the relevant optic features a significant magnification. Consequently the depth of field is relatively small. If this depth of field is smaller than the distance error which can occur for the distance between lens and object this leads to partly unsharp images. It is precisely in the inspection of large surfaces of an object that these distance tolerances arise to a greater extent. These distance errors are produced overall by plane-parallelism errors in the inspection table, object holder, for example chuck, and object in relation to the focus plane of a lens of a measuring head.

Previously known systems are essentially designed for the inspection of small surfaces of an object. In this case the image is focused using autofocus operation of a microscope of an inspection unit. Another option is to move the lens into the focused position. This involves fitting an adapter ring with an adjusting element between the lens and the microscope body. The adapter ring allows the distance between object and lens to be adjusted in such a way that the image is focused. A further option is to move the microscope manually, using an adjusting wheel for example, with the distance between lens and surface of an object being corrected so that the overhead view of the object plane is displayed sharply in the eyepiece or the camera chip of a camera connected downstream from the optics. For inspection of smaller object surfaces one-off focusing is sufficient as a rule.

SUMMARY OF THE INVENTION

An object of the invention is to provide a method and a device for plane-parallel orientation of a level extended object surface to a focus plane of a lens.

The invention is based on the knowledge that with a device and with a method corresponding to this patent application extensive, essentially flat areas can be optically inspected by a measuring head, with this being positioned at right angles to the axis of the optics present in the measuring head and with the features of the invention, allowing a very precise adjustment of the plane-parallelism between the focus plane of the optics and the surface to be measured to be achieved. In This case the elements of the device are provided to accept a flat extended body, for example a wafer or a frame, to hold it and for inspection of this extensive surface, to move it relative to a measuring head and possibly with its distance measurement system laterally in the x and y direction. For each state to be assumed here the current surface Image recording must be adjusted to be optically sharp.

By using three adjustment drives the adjustments to achieve plane-parallelism between the focus plane and the object surface are achieved. The adjustment drives, especially embodied as piezo actors, feature a typical adjustment range of 100 to 400 μm. An adjustment is made in the z direction which corresponds to changing a height value.

For each of the variants envisaged in the invention as a first step for all three surface points over which advantageously at least three adjustment drives are located in each case are focused using the optics of the measuring head and stored. To this end the measuring head his moved laterally over the relevant points and subsequently the adjustment elements lying below are adjusted in the z direction in such a way that optical focusing is achieved. If this process is executed at for example 3 adjustment elements on the surface to be inspected above them, this means for the object surface an overall plane-parallel alignment to a focus plane of the optics. Starting from this state in which the plane-parallelism of the planes is established only the surface of an object can be inspected.

Further indentations or protrusions on the surface of the object can require further error corrections. In an advantageous way a grid of support points is established on the surface in this way before the surface is inspected, in which case, for each support point the x, y data is known and using the equal height correction of all adjustment elements the system is moved to a z position of the current support point, which corresponds to optical focusing. Through this grid of support points which are known to the system error correction can be applied to sections for topographical errors on the object.

The advantageous use of a distance measurement system connected in parallel to the measuring head and also aligned to the surface of an object makes recording a grid of support points superfluous. After the first procedural step described above for plane-parallel adjustment of the surface of an object to a focus plane of the optics of the measuring head the distance to a measuring point with known x, y co-ordinate will be determined at regular intervals using the distance measurement system, in which case, during the relative movement between distance measuring system and measuring head on the one side and between the surface of an object first the measuring point is processed by the distance measurement system and through the available relative speed of movement and through the distance present between distance measurement system and measuring head the measuring head reaches the measuring point for inspection after a delay. This means that the distance measuring system can regularly determine new measuring points which, if they do not lie within an allowed range of tolerances, make it possible to correct errors.

Control is via the image information from a 2D camera or 1D camera, for example a scanning camera using contrast measurement. In this case the Area of Interest (AOI) is used in which the objects or parts of objects of interest lie. In this way, even if the height of the objects of interest shifts compared to their surroundings there is still sharp focusing.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
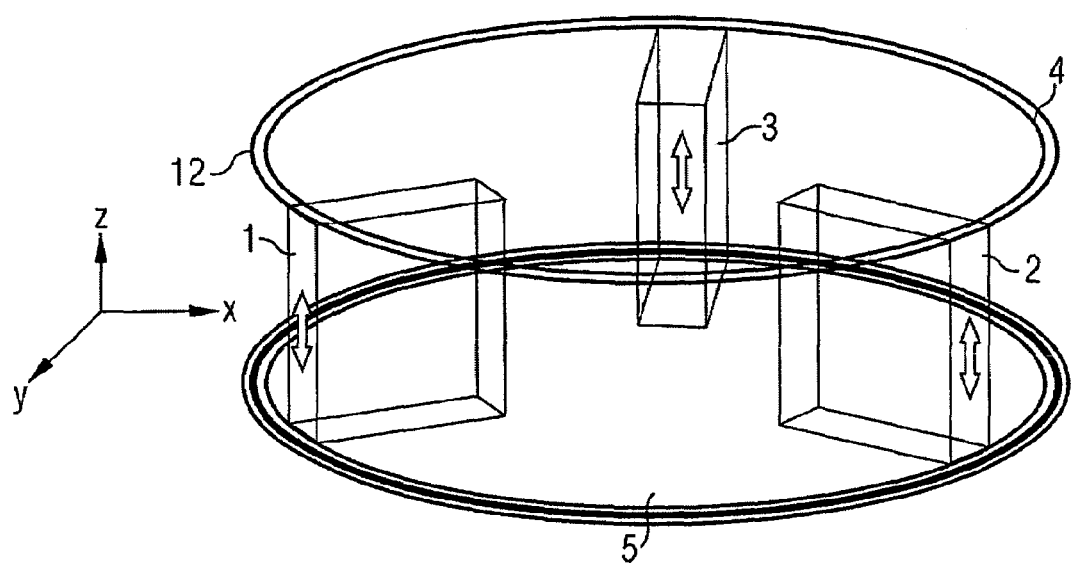
FIG. 1 is a schematic perspective view of a holder device for holding flat-profile objects, used for wafer inspection for example.
Figure 2:
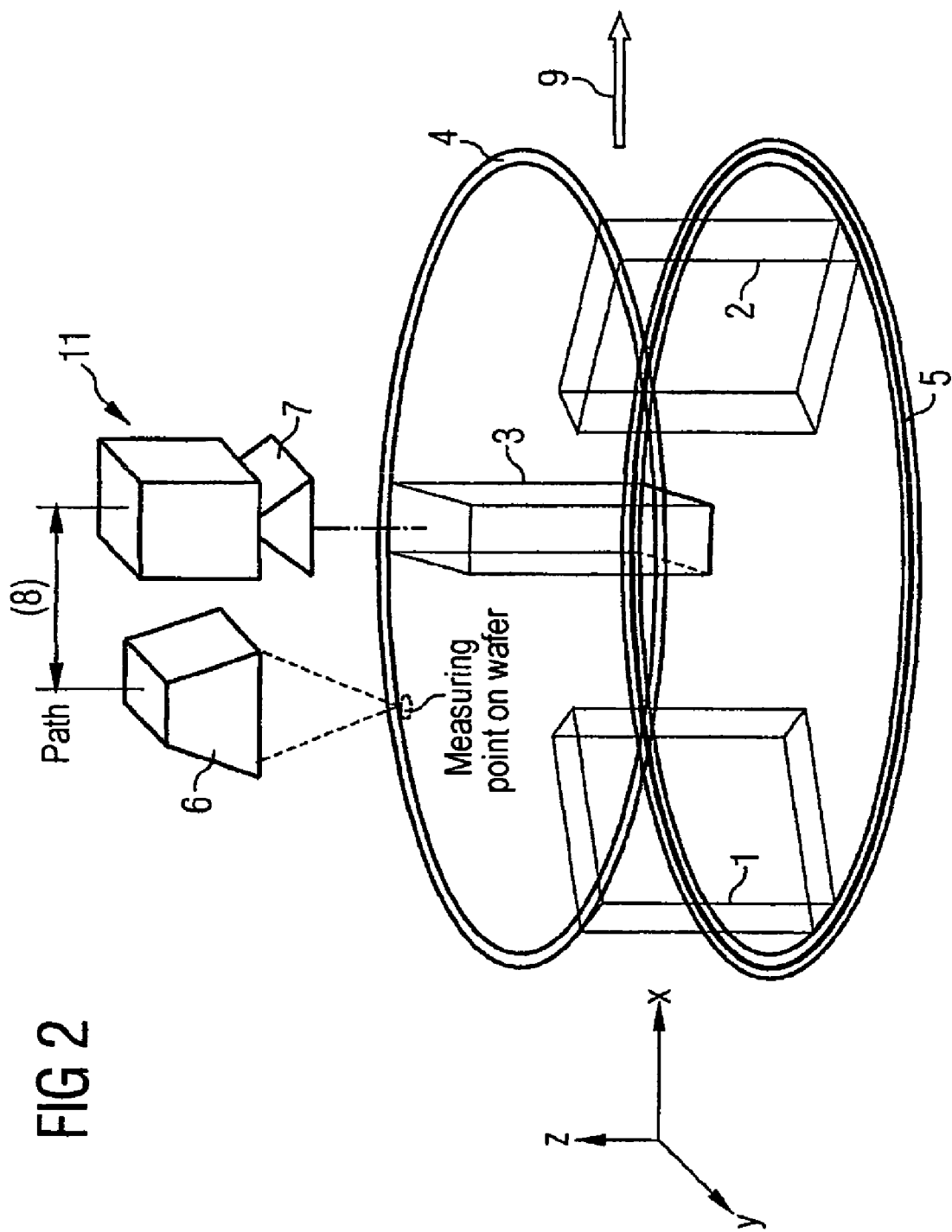
FIG. 2 is a schematic perspective view of the entire inspection system with measuring head and optics, distance measurement system and piezo actors.

Reference will now be made in detail to the preferred embodiments of the present invention, examples of which are illustrated in the accompanying drawings, wherein like reference numerals refer to like elements throughout.

A system for inspection of wafer surfaces is described which allows a high-precision following of the surface of an object with an accuracy within the required depth of field. Tilting of the measuring table used can be compensated for, so that even within the image recorded the entire image area is sharp. In particular for inspection of larger surfaces with high inspection speed this method presented is superior to the optical autofocus principle or manual focusing.

To obtain plane-parallelism between a surface of an object and a focus plane of a lens in the measuring head, at least three adjustment elements, for example piezo actors 1, 2, 3 are used. Here the adjustment elements are integrated into the object holder. The object holder is for example represented by a chuck having upper and lower chuck plates. The adjusting elements 1, 2, 3, represented by piezo actors are connected in between.

To set the plane-parallelism between focus plane and surface of an object, first, as part of a preliminary measurement, the object holder with the object is moved below the lens in such a way that the lens 7 is positioned over a piezo actor. By moving the piezo actor above which the lens is currently positioned focusing is achieved, i.e. the image that is produced in the camera in measuring head 11 is sharply focused. This process is repeated for each piezo actor or for a support point which is defined above the support surface of the object on the piezo actor. With this first procedural step the piezo actors are adjusted individually in such a way that when a support point is sharply focused the associated piezo actor moves the support point. Into the depth of field of lens 7. After this routine is executed all errors which are generated by errors in the plane-parallelism are eliminated. Plane-parallelism is taken to mean the parallelism of two flat surfaces.

To control the object holder, the chuck, electronics are used which are at least partly accommodated in the object holder. This electronics includes for example the measurement amplifier for the integrated error correction of the adjusting elements, as well as the control system for these elements. The characteristics of these adjusting elements are as a rule not susceptible to hysteresis, so that for example a voltage applied to a piezo actor corresponds to an exact elongation of this actor.

To establish the plane-parallelism between focus plane and surface of an object at least three different randomly selected positions on the surface of an object can be selected. In principle adjustment with or without an object is possible, so that for example for the case in which the upper chuck plate 4 is not carrying an object the plane-parallelism between focus plane and upper chuck plate 4 can be established. This could be of importance for the case where a non-plane-parallel wafer is to be milled plane-parallel. Thus initially by the plane-parallel orientation of the upper side of the upper chuck 4 one side of a wafer lying on it is aligned so that it is plane-parallel. The upper side of a wafer moving at an angle to this can now be corrected.

An object 12 can be a wafer or a frame, with a frame being represented by a tensioning ring, with a wafer being glued to a foil.

The surface aligned after the first important procedural step is sampled in different positions within the context of a preliminary measurement and the measured values are used as a support points to determine the position of the surface of an object. The object is positioned over the measuring point. The image sharpness is measured and if the image is unsharp the entire object holder is raised or lowered evenly over the adjustment elements, piezo actors until the image is sharp. The z-position determined in this way is assigned to the support point. Using the support points thus determined a measurement path via x, y, z is determined for inspection of the object. The distance tolerances at and around the measuring point within the depth of field of the object lie in this path.

With an additional use of a distance measurement system which operates in conjunction with the adjustment elements and is arranged alongside the measuring head with the lens there is a further option for on-line correction, i.e. correction during operation. With this distance measuring system a unique distance measurement between lens and surface of an object or between lens and object holder is possible. If the object or an object point lies within the depth of field of the lens, with adjustment being undertaken via the adjustment elements, the measured value of the distance measurement system, is stored together with the lateral coordinates of the current measurement point as an operating point. With a subsequent calibration of an object the object holder is always moved in such a way over the piezo actors in connection with an internal adjustment that the operating point defined before the beginning of the measurement which represents a required value is also retained during the measurement. This means that the difference between the distance value recorded during the measurement, which corresponds to the actual value and the defined operating point, the required value is adjusted to a minimum.

The distance measurement system relative to the movement of a point on the surface below measuring head 11 is positioned in such a way relative to measuring head 11 that any point on the surface of the object obtained during an inspection first passes the distance measurement system and then, after a specific distance 8, which corresponds to the distance between the distance measurement system and the measuring head, appears under the measuring head 11. This means that points which were recorded by the distance measuring system are only recorded by the lens 7 of the measuring head 11 after a specific time with can be calculated from the path 8 and the speed of movement. The values determined by the distance measurement system are issued to the adjustment system after a delay so that the correction via the adjustment elements is then undertaken when the lens 7 travels over the measuring point. By using a number of distance sensors 6 tilting can be measured and corrected. Each adjustment element has its own control system so that for example a temperature drift can be compensated for.

The invention has been described in detail with particular reference to preferred embodiments thereof and examples, but it will be understood that variations and modifications can be effected within the spirit and scope of the invention.

The invention claimed is:

1. A device for optical inspection of a flat surface of an object, said device comprising:
   a measuring head comprising a lens;
   a lower object carrier; and
   an upper object carrier provided for holding the object, said upper object carrier being supported by at least three support places with adjustment drives providing at least two of the three support places, the adjustment drives being provided to operate in conjunction and engagement with said lower object carrier so as to obtain a plane-parallel orientation between a level surface of said upper object carrier and a focus plane of said lens, said measuring head being positioned above a surface of said upper object carrier, said measuring head and said upper object carrier being provided to be moved relative to each other for adjustment with respect to each other, said measuring head being provided for sampling the surface of the object when applied on said upper object carrier in a focus area of the lens, said adjustment drives being provided for adjusting the at least two of the three support places in order to bring said upper object carrier within the focus area of the lens, said adjustment drives being further provided for adjusting the at least two of the three support places for said object when applied on said upper object carrier within the focus area of the lens.

2. A device in accordance with claim 1, in which the adjustment drives engage at the at least three support places.

3. A device in accordance with claim 2, further comprising a distance measurement system, spaced from and fixed to said measuring head in orientation to the surface of the object, through which distance values can be determined with a given focusing of object surface areas.

4. A device in accordance with claim 3, wherein the adjustment drives are piezo actors.

5. A method of optical inspection of a flat surface of an object, comprising:
   adjusting an object surface of an object held in an upper object holder supported at support points by at least three adjustment drives evenly distributed between the upper object holder and a lower object holder so as to obtain a carrying the upper object holder plane-parallel orientation between a level surface of said upper object carrier and the focus plane of the lens, the object surface being adjusted relative to a measuring head associated with the lens by adjusting a height value of each of the adjustment drives when a corresponding support point is positioned below the measuring head during optically sham setting to orient the object surface plane-parallel to the focus plane of the lens; wherein at least three random different positions on the surface of the object are used as measurement locations; and wherein the support points within a specified grid on the object surface with even changes in height of the object surface are each sharply focused and calibrated relative to their height.

6. A method in accordance with claim 5, further comprising
   determining, one of continuously and discretely within a system-controlled time interval, a difference between a required value and an actual distance measured by an additional distance measurement system set optically sharp for each of a plurality of operating points; and
   readjusting the height value of the adjustment drives by a controller in response to the difference determined using the additional distance measurement system to maintain orientation of the object surface plane-parallel to the focus plane of the lens.

7. A method in accordance with claim 5, further comprising repeating said determining, using a plurality of distance measurement systems, and said readjusting to correct tilting of the object surface.

* * * * *